(12) United States Patent
Ishizuki et al.

(10) Patent No.: US 8,995,709 B2
(45) Date of Patent: Mar. 31, 2015

(54) METHOD FOR CALCULATING WEIGHT RATIO BY QUALITY GRADE IN GRAIN APPEARANCE QUALITY GRADE DISCRIMINATION DEVICE

(75) Inventors: Hiroki Ishizuki, Tokyo (JP); Takayuki Emori, Tokyo (JP); Yoshihisa Nakata, Tokyo (JP)

(73) Assignee: Satake Corporation (JP)

(*) Notice: Subject to any disclaimer, the term of this patent is extended or adjusted under 35 U.S.C. 154(b) by 0 days.

(21) Appl. No.: 13/639,270

(22) PCT Filed: May 10, 2011

(86) PCT No.: PCT/JP2011/002583
§ 371 (c)(1),
(2), (4) Date: Oct. 4, 2012

(87) PCT Pub. No.: WO2011/145287
PCT Pub. Date: Nov. 24, 2011

(65) Prior Publication Data
US 2013/0051622 A1 Feb. 28, 2013

(30) Foreign Application Priority Data
May 19, 2010 (JP) .................................. 2010-115425

(51) Int. Cl.
*G06K 9/00* (2006.01)
*G01N 21/84* (2006.01)
*G01N 21/85* (2006.01)

(52) U.S. Cl.
CPC ................ *G01N 21/84* (2013.01); *G01N 21/85* (2013.01); *G01N 2021/8466* (2013.01)
USPC ............................................................ 382/100

(58) Field of Classification Search
None
See application file for complete search history.

(56) References Cited

U.S. PATENT DOCUMENTS

2003/0048927 A1    3/2003  Sato et al. .................... 382/110

FOREIGN PATENT DOCUMENTS

| JP | 7-33151 | 7/1995 | ............ G01N 21/85 |
| JP | 2000-206054 | 7/2000 | ............ G01N 21/88 |

(Continued)

OTHER PUBLICATIONS

Yadav ("Monitoring Milling quality of rice by image analysis", 2001).*

(Continued)

*Primary Examiner* — Avinash J Yentrapati
(74) *Attorney, Agent, or Firm* — Hayes Soloway P.C.

(57) ABSTRACT

A method is provided for calculating a weight ratio by quality grade using a grain appearance quality grade discrimination device. The method involves the steps of imaging a plurality of grains; discriminating the quality grade of the grains on the basis of data of the imaged grains; tallying, by quality grade, the number of pixels in said data of the imaged grains with regards to the grains whose quality grade has been discriminated; multiplying the number of pixels tallied by quality grade by a weight conversion coefficient per pixel predetermined by quality grade, and thereby converting said number of pixels into a weight by quality grade; and calculating the weight ratio by quality grade of the grains on the basis of the weight by quality grade.

3 Claims, 10 Drawing Sheets

(56) References Cited

FOREIGN PATENT DOCUMENTS

| | | | | |
|---|---|---|---|---|
| JP | 2003-090799 | 3/2003 | ............ | G01N 21/85 |
| JP | 2003-090800 | 3/2003 | ............ | G01N 21/85 |
| JP | 2003-098096 | 4/2003 | ............ | G01N 21/85 |
| JP | 2008-298695 | 12/2008 | ............ | G01N 21/85 |
| KR | 20090033568 | 4/2009 | ............ | G01B 11/00 |
| KR | 10 0925209 | 10/2009 | ............ | B07C 5/342 |
| TW | 201013184 | 4/2010 | ............ | G01N 33/02 |
| WO | WO 2009/045035 | 4/2009 | ............ | G01N 21/85 |

OTHER PUBLICATIONS

International Search Report issued in PCT/JP11/002583 on Jul. 5, 2011, with English translation, 4 pgs.

Chinese Office Action issued in Chinese Appln. No. 201180033085.8 on Aug. 26, 2013, with English translation, 7 pgs.

Korean Office Action issued in Korean Appln. No. 10/2012/7025990 on Jan. 3, 2014, with English translation, 5 pgs.

Taiwanese Office Action (with translation) issued in related application No. 10115198, dated Dec. 16, 2014 (5 pgs).

* cited by examiner

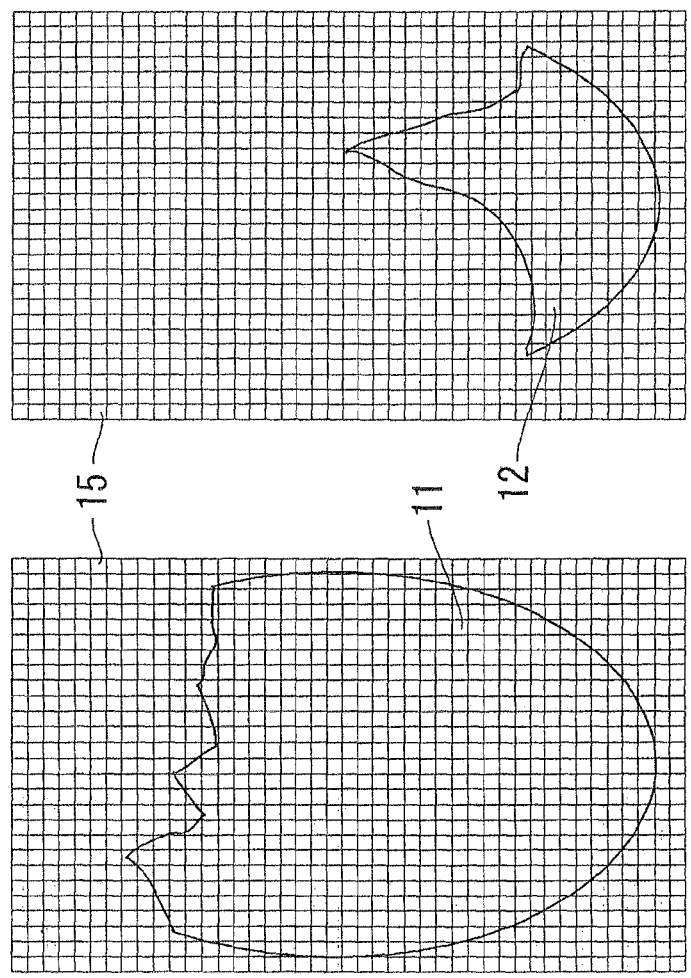

Fig.4  COUNTRY OF EVALUATION: JAPAN, GRAIN: UNPOLISHED RICE

| DISCRIMINATION CLASSIFICATION (QUALITY GRADE) | NUMBER OF DOTS | | WEIGHT CONVERSION COEFFICIENT (DOT WEIGHT) | | CONVERTED WEIGHT (g) | | WEIGHT RATIO (%) |
|---|---|---|---|---|---|---|---|
| WELL-ORDERED KERNELS | 1102478 | | 0.0000120124 | | 13.24344095 | | 58.5 |
| MILKY WHITE KERNELS | 175777 | | 0.0000114268 | | 2.008564718 | | 8.9 |
| IMMATURE BASE KERNELS | 79295 | | 0.0000113557 | | 0.900449358 | | 4.0 |
| IMMATURE ABDOMINAL WHITE KERNELS | 41919 | | 0.0000114257 | | 0.478953034 | | 2.1 |
| GREEN IMMATURE KERNELS | 51000 | | 0.0000111050 | | 0.566353166 | | 2.5 |
| OTHER IMMATURE KERNELS | 202000 | × | 0.0000111950 | = | 2.261387362 | → | 10.0 |
| BROKEN KERNELS | 3474 | | 0.0000110305 | | 0.038319785 | | 0.2 |
| CRACKED-GERM KERNELS | 103856 | | 0.0000119430 | | 1.240355355 | | 5.5 |
| SPROUTING KERNELS | 19394 | | 0.0000110396 | | 0.214101518 | | 0.9 |
| DEGENERATED SPROUT KERNELS | 18385 | | 0.0000108476 | | 0.199433718 | | 0.9 |
| RUSTY KERNELS | 13995 | | 0.0000113051 | | 0.158214445 | | 0.7 |
| BLEMISHED KERNELS | 19393 | | 0.0000118396 | | 0.229605089 | | 1.0 |
| INSECT-DAMAGED KERNELS | 0 | | 0.0000112950 | | 0 | | 0.0 |
| DISEASED KERNELS | 0 | | 0.0000119406 | | 0 | | 0.0 |
| DEFORMED KERNELS | 22034 | | 0.0000118737 | | 0.261624092 | | 1.2 |
| OTHER DAMAGED KERNELS | 0 | | 0.0000117377 | | 0 | | 0.0 |
| GREEN DEAD-KERNEL RICE | 39495 | | 0.0000083887 | | 0.33131107 | | 1.5 |
| WHITE DEAD-KERNEL RICE | 24065 | | 0.0000083887 | | 0.201873678 | | 0.9 |
| COMPLETELY DISCOLORED KERNELS | 12355 | | 0.0000109849 | | 0.13571794 | | 0.6 |
| PARTIALLY DISCOLORED KERNELS | 15242 | | 0.0000113960 | | 0.173697231 | | 0.8 |
| RED RICE | 0 | | 0.0000112941 | | 0 | | 0.0 |
| TOTAL | 1944157 | | | | TOTAL WEIGHT (g) 22.64340251 | | TOTAL (%) 100.0 |

Fig.5A (a) COUNTRY OF EVALUATION: JAPAN, GRAIN: POLISHED RICE

| DISCRIMINATION CLASSIFICATION (QUALITY GRADE) | NUMBER OF DOTS |
|---|---|
| PERFECT KERNELS | 1008901 |
| CRACKED-GERM KERNELS | 102030 |
| BROKEN KERNELS | 43653 |
| POWDERY KERNELS | 32524 |
| WHITE-BACKED KERNELS | 45664 |
| CHIPPED KERNELS | 45033 |
| OTHER DAMAGED KERNELS | 23011 |
| hemiptera | 3533 |
| aphelenchoides besseyi | 4343 |
| COMPLETELY DISCOLORED KERNELS | 5324 |
| FOREIGN SPECIES | 4343 |
| FOREIGN OBJECT | 2456 |
| TOTAL | 1320815 |

×

| WEIGHT CONVERSION COEFFICIENT (DOT WEIGHT) |
|---|
| 0.000011999 |
| 0.000011344 |
| 0.000011432 |
| 0.000010299 |
| 0.000011222 |
| 0.000010929 |
| 0.000011323 |
| 0.000011543 |
| 0.000011321 |
| 0.000010737 |
| 0.000011245 |
| 0.000010432 |

=

| CONVERTED WEIGHT (g) |
|---|
| 12.1058031 |
| 1.157428032 |
| 0.499041096 |
| 0.334964676 |
| 0.512441408 |
| 0.492165657 |
| 0.260553553 |
| 0.0407811419 |
| 0.049167103 |
| 0.057163788 |
| 0.048837035 |
| 0.025620992 |
| TOTAL WEIGHT (g) 15.58396815 |

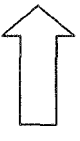

| WEIGHT RATIO (%) |
|---|
| 77.7 |
| 7.4 |
| 3.2 |
| 2.1 |
| 3.3 |
| 3.2 |
| 1.7 |
| 0.3 |
| 0.3 |
| 0.4 |
| 0.3 |
| 0.2 |
| TOTAL (%) 100.0 |

Fig. 5B  (b) COUNTRY OF EVALUATION: CHINA, GRAIN: UNPOLISHED RICE

| DISCRIMINATION CLASSIFICATION (QUALITY GRADE) | NUMBER OF DOTS |
|---|---|
| WELL-ORDERED UNPOLISHED RICE | 1009901 |
| BROKEN RICE | 102530 |
| INCOMPLETE KERNELS | 43753 |
| IMMATURE KERNELS | 42524 |
| DISEASE-BLEMISHED KERNELS | 45864 |
| MOLDY KERNELS | 45233 |
| SPROUTED KERNELS | 23311 |
| INSECT-DAMAGED KERNELS | 3533 |
| FOREIGN OBJECTS | 4265 |
| TOTAL | 1320914 |

×

| WEIGHT CONVERSION COEFFICIENT (DOT WEIGHT) |
|---|
| 0.000013899 |
| 0.000013244 |
| 0.000013332 |
| 0.000012199 |
| 0.000012122 |
| 0.000013829 |
| 0.000012223 |
| 0.000013443 |
| 0.00002145 |

=

| CONVERTED WEIGHT (g) |
|---|
| 14.036614 |
| 1.35790732 |
| 0.583314996 |
| 0.518750276 |
| 0.555963408 |
| 0.625527157 |
| 0.284930353 |
| 0.047494119 |
| 0.09148425 |
| TOTAL WEIGHT (g) 18.10198588 |

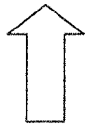

| WEIGHT RATIO (%) |
|---|
| 77.5 |
| 7.5 |
| 3.2 |
| 2.9 |
| 3.1 |
| 3.5 |
| 1.6 |
| 0.3 |
| 0.5 |
| TOTAL (%) 100.0 |

Fig.5C (c) COUNTRY OF EVALUATION: CHINA, GRAIN: POLISHED RICE

| DISCRIMINATION CLASSIFICATION (QUALITY GRADE) | NUMBER OF DOTS | | WEIGHT CONVERSION COEFFICIENT (DOT WEIGHT) | | CONVERTED WEIGHT (g) | WEIGHT RATIO (%) |
|---|---|---|---|---|---|---|
| WELL-ORDERED POLISHED RICE | 1009901 | | 0.000011999 | | 12.1178021 | 59.8 |
| BROKEN RICE | 102530 | | 0.000011344 | | 1.16310032 | 5.7 |
| LARGE BROKEN RICE | 43753 | | 0.000011432 | | 0.500184296 | 2.5 |
| SMALL BROKEN RICE | 42524 | × | 0.000010299 | = | 0.437954676 | 2.2 |
| INCOMPLETE KERNELS | 45864 | | 0.000011222 | | 0.514685808 | 2.5 |
| IMMATURE KERNELS | 45233 | | 0.000010929 | | 0.494351457 | 2.4 |
| DISEASE-BLEMISHED KERNELS | 23311 | | 0.000011323 | | 0.263950453 | 1.3 |
| INSECT-DAMAGED KERNELS | 3533 | | 0.000011543 | | 0.040781419 | 0.2 |
| MOLDY KERNELS | 4265 | | 0.000011321 | | 0.048284065 | 0.2 |
| UNPOLISHED RICE IN POLISHED RICE | 5315 | | 0.000010737 | | 0.057067155 | 0.3 |
| MILKY WHITE RICE | 314351 | | 0.000011245 | | 3.534876995 | 17.5 |
| YELLOWED RICE | 32131 | | 0.000010432 | | 0.335190592 | 1.7 |
| FOREIGN OBJECT | 31231 | | 0.000021455 | | 0.66990495 | 3.3 |
| FOREIGN SPECIES | 3211 | | 0.000024321 | | 0.078094731 | 0.4 |
| TOTAL | 1707153 | | | TOTAL WEIGHT (g) | 20.25622902 | |

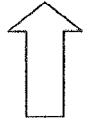

| TOTAL (%) | 100.0 |
|---|---|

Fig.7 COUNTRY OF EVALUATION: JAPAN, GRAIN: UNPOLISHED RICE - PRIOR ART

| DISCRIMINATION CLASSIFICATION (QUALITY GRADE) | NUMBER OF GRAINS |
|---|---|
| WELL-ORDERED KERNELS | 730 |
| MILKY WHITE KERNELS | 36 |
| IMMATURE BASE KERNELS | 15 |
| IMMATURE ABDOMINAL WHITE KERNELS | 12 |
| GREEN IMMATURE KERNELS | 50 |
| OTHER IMMATURE KERNELS | 100 |
| BROKEN KERNELS | 5 |
| CRACKED-GERM KERNELS | 10 |
| SPROUTING KERNELS | 1 |
| DEGENERATED SPROUT KERNELS | 0 |
| RUSTY KERNELS | 4 |
| BLEMISHED KERNELS | 2 |
| INSECT-DAMAGED KERNELS | 0 |
| DISEASED KERNELS | 0 |
| DEFORMED KERNELS | 10 |
| OTHER DAMAGED KERNELS | 0 |
| GREEN DEAD-KERNEL RICE | 10 |
| WHITE DEAD-KERNEL RICE | 12 |
| COMPLETELY DISCOLORED KERNELS | 2 |
| PARTIALLY DISCOLORED KERNELS | 1 |
| RED RICE | 0 |
| TOTAL | 1000 |

×

| WEIGHT CONVERSION COEFFICIENT (SINGLE-GRAIN WEIGHT) |
|---|
| 0.02187 |
| 0.01849 |
| 0.01909 |
| 0.01866 |
| 0.019 |
| 0.01786 |
| 0.01385 |
| 0.02144 |
| 0.02057 |
| 0.01903 |
| 0.02 |
| 0.01789 |
| 0.01727 |
| 0.02 |
| 0.01794 |
| 0.01746 |
| 0.01278 |
| 0.0153 |
| 0.02 |
| 0.01788 |
| 0.02 |

=

| CONVERTED WEIGHT (g) | WEIGHT RATIO (%) |
|---|---|
| 15.9651 | 76.6 |
| 0.66564 | 3.2 |
| 0.28635 | 1.4 |
| 0.22392 | 1.1 |
| 0.95 | 4.6 |
| 1.786 | 8.6 |
| 0.06925 | 0.3 |
| 0.2144 | 1.0 |
| 0.02057 | 0.1 |
| 0 | 0.0 |
| 0.08 | 0.4 |
| 0.03578 | 0.2 |
| 0 | 0.0 |
| 0 | 0.0 |
| 0.1794 | 0.9 |
| 0 | 0.0 |
| 0.1278 | 0.6 |
| 0.1836 | 0.9 |
| 0.04 | 0.2 |
| 0.01788 | 0.1 |
| 0 | 0.0 |

| TOTAL WEIGHT (g) | 20.84569 | TOTAL (%) | 100.0 |
|---|---|---|---|

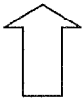

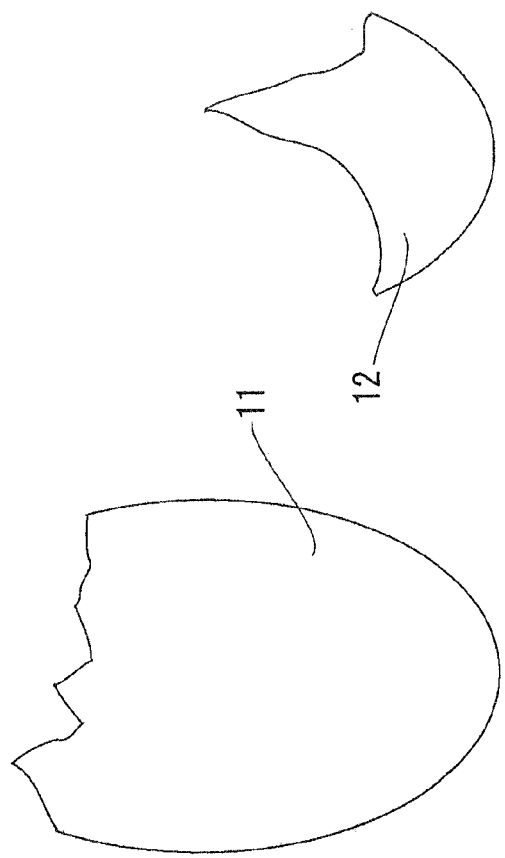
Fig.8 (a) PRIOR ART
Fig.8 (b) PRIOR ART

METHOD FOR CALCULATING WEIGHT RATIO BY QUALITY GRADE IN GRAIN APPEARANCE QUALITY GRADE DISCRIMINATION DEVICE

TECHNICAL FIELD

The present invention relates to a method for calculating the weight ratio by quality grade of rice, wheat, beans, corn, or other grains in a grain appearance quality grade discrimination device.

BACKGROUND ART

Known techniques for evaluating rice and other grains include evaluation by appearance quality grade. This evaluation is performed on the basis of the well-ordered kernel percentage, which is the weight ratio of well-ordered kernels among the grains, or the weight ratio by appearance quality grade of the grains.

In order to calculate each of the above-mentioned weight ratios, it is necessary to sort, grain by grain, the grains that have been hulled into well-ordered kernels and waste kernels, or into well-ordered kernels and cracked-germ kernels, immature kernels, dead kernels, colored kernels, damaged kernels other than cracked-germ kernels, and the like; and to weigh the sorted grains. The calculation is therefore cumbersome and time-consuming.

Therefore, there is a known technique in which a grain appearance quality grade discrimination device is used to calculate the weight ratio by quality grade of grains.

The grain appearance quality grade discrimination device is a device in which, e.g., a scanner is used to simultaneously image about 1000 sample grains, and image information obtained by the imaging is used to discriminate the quality grade of individual sample grains; and in which it is possible to readily evaluate the quality grade of edible grains (see Patent Citation 1, 2).

FIG. 6 shows a conventional workflow for using a grain appearance quality grade discrimination device according to Patent Citation 1 to calculate the weight ratio by quality grade of grains.

(1) Imaging Processing (S11)
The grain appearance quality grade discrimination device images sample grains of the grains to be evaluated and acquires imaging data for the sample grains.

(2) Data Processing (S12)
The grain appearance quality grade discrimination device extracts data relating to the quality grade of the sample grains on the basis of the imaging data.

(3) Quality Grade Discrimination Processing (S13)
The grain appearance quality grade discrimination device compares the data relating to the quality grade of the sample grains to a threshold value that has been predetermined, and thereby discriminates the quality grade of the sample grains.

(4) Grain Number Tallying Processing (S14)
The grain appearance quality grade discrimination device tallies grain numbers by quality grade with regards to the sample grains whose quality grade has been discriminated.

(5) Weight Ratio Calculation Processing (S15)
The grain appearance quality grade discrimination device calculates the weight ratio by quality grade on the basis of grain numbers of the sample grains tallied by quality grade and a weight conversion coefficient per grain (single-grain weight) that has been set for each quality grade in advance.

(6) Output Processing (S16)
The grain appearance quality grade discrimination device outputs, to a printer or a monitor, a calculated value of the weight ratio by quality grade of the sample grains.

FIG. 7 shows an example of calculating the weight ratio by quality grade of unpolished rice grains according to the above-mentioned conventional method. In FIG. 7, the quality grade of the unpolished rice grains is represented as "discrimination classification".

As described further above, in the grain appearance quality grade discrimination device, a weight conversion coefficient per grain (single-grain weight) of unpolished rice is predetermined for each of the discrimination classifications (quality grades).

The grain appearance quality grade discrimination device then multiplies a grain number of sample grains tallied by discrimination classification (quality grade) by the weight conversion coefficient (single-grain weight), and thereby obtains a converted weight. Then, a proportion of the converted weight in relation to a total weight is calculated as the weight ratio by discrimination classification (quality grade).

According to a method in which the above-mentioned grain appearance quality grade discrimination device is used, it is possible to calculate the weight ratio by quality grade of grains in a simple and speedy manner.

When grains are observed in detail, individual sizes differ amongst grains that are classified into the same quality grade.

FIG. 8 shows an example of comparing two broken grains.
The broken grain shown in FIG. 8(*a*) and the broken grain shown in FIG. 8(*b*) clearly differ in size.

However, the method in which the above-mentioned conventional grain appearance quality grade discrimination device is used is one in which both grains are treated as a single broken grain and the converted weight is obtained by performing a multiplication using the same weight conversion coefficient (single-grain weight); it is not necessarily possible to calculate the weight ratio in an accurate manner.

PRIOR ART CITATIONS

Patent Citations

Patent Citation 1: JP-A 2003-90799
Patent Citation 2: Examined Utility Model Application Publication No. 7-33151

DISCLOSURE OF THE INVENTION

Problem to be Solved by the Invention

Therefore, an object of the present invention is to provide a method according to which it is possible to calculate accurately the weight ratio by quality grade of rice, wheat, beans, corn, or other grains, even in an instance in which a grain appearance quality grade discrimination device is used to calculate the weight ratio.

Means for Solving the Problem

In order to achieve the above-mentioned object, the present invention is a method for calculating a weight ratio by quality grade using a grain appearance quality grade discrimination device for imaging grains using imaging means and discriminating the quality grade of the grains on the basis of data of the imaged grains; the method for calculating a weight ratio by quality grade using a grain appearance quality grade discrimination device characterized in comprising: imaging a plurality of grains; discriminating the quality grade of the grains on the basis of data of the imaged grains; tallying, by quality grade, the number of pixels in the data of the imaged grains with regards to the grains whose quality grade has been discriminated; multiplying the number of pixels tallied by quality grade by a weight conversion coefficient per pixel predetermined by quality grade, and thereby converting the number of pixels into a weight by quality grade; and calculating the weight ratio by quality grade of the grains on the basis of the weight by quality grade.

In the method for calculating a weight ratio by quality grade using a grain appearance quality grade discrimination device according to the present invention, the imaging means for imaging the grains is preferably an image-reading device.

Effect of the Invention

The method for calculating the weight ratio by quality grade using the grain appearance quality grade discrimination device according to the present invention is one in which the number of pixels in the imaging data for the grains is tallied by quality grade; the number of pixels tallied by quality grade is multiplied by the weight conversion coefficient per pixel predetermined by quality grade, whereby the number of pixels is converted into a weight by quality grade; and the weight ratio by quality grade is calculated on the basis of the weight by quality grade. Therefore, it is possible to reflect the grain size in an appropriate manner during conversion of the weight by quality grade, and to calculate the weight ratio by quality grade of the grains in a more accurate manner than according to conventional methods.

In the method for calculating the weight ratio by quality grade using the grain appearance quality grade discrimination device according to the present invention, if the imaging means for imaging the grains is an image-reading device, a plurality of grains can be simultaneously imaged, and it is therefore possible to calculate the weight ratio by quality grade of the grains in a simple and speedy manner.

BRIEF DESCRIPTION OF THE DRAWINGS

FIGS. 3(a) and 3(b) show a comparison of broken grains whose sizes differ, made at pixel level;

FIG. 4 is an example of calculating the weight ratio by quality grade of unpolished rice according to the method of the present invention;

FIGS. 5(a), 5(b) and 5(c) are examples of calculating the weight ratio by quality grade of unpolished rice and polished rice according to the method of the present invention;

FIG. 7 is an example of calculating the weight ratio by quality grade of unpolished rice according to a conventional method; and FIGS. 8(a) and 8(b) show a comparison of broken grains whose sizes differ.

BEST MODE FOR CARRYING OUT THE INVENTION

A description will now be given of an embodiment of the present invention with reference to the accompanying drawings.

Figure 1A:
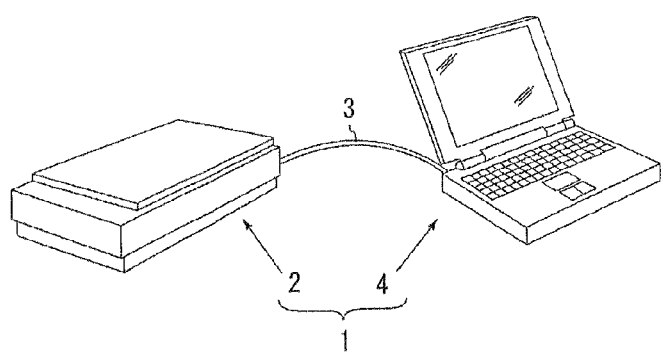
FIGS. 1(a) and 1(b) are external views showing an example of a grain appearance quality grade discrimination device used in the method of the present invention.
Figure 1B:
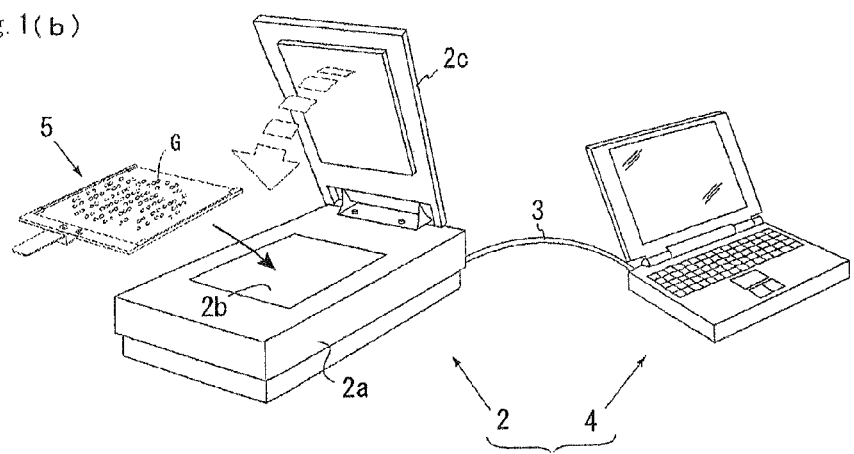

FIG. 1 shows an example of a grain appearance quality grade discrimination device used in the method of the present invention.

A grain appearance quality grade discrimination device 1 comprises imaging means 2 for imaging rice, wheat, bean, corn, or another grain, and quality grade discrimination means 4 connected to the imaging means 2 by a cable 3. For example, a commercially available scanner can be used for the imaging means 2. A Personal Computer (PC) can be used for the quality grade discrimination means 4.

The imaging means 2 comprises a main body 2a, an imaging platform 2b provided to an upper surface of the main body 2a, and a cover 2c for opening and closing an upper surface of the imaging platform 2b. The main body 2a comprises a white fluorescent lamp, a white LED, or another light source for emitting light onto a grain placed on the imaging platform 2b; and a light receiver, made from a color CCD line sensor or a similar device, for receiving light reflected by the grain. The grains G are arranged in a row and accommodated on an imaging tray 5, and placed on the imaging platform 2b.

The quality grade discrimination means 4 comprises:

an image processor for performing image processing on imaging data of the grain imaged by the imaging means 2 and extracting color and other optical information, profile and other shape information, and other information relating to the grain; a computation controller in which there has been stored and configured in advance a threshold value, for a comparison to be made with each of the information extracted by the image processor and discriminating the quality grade of the grain, and a weight conversion coefficient (dot weight) per pixel, for calculating the weight ratio by quality grade of the grain; and a display for displaying results obtained by the computation controller.

The grain appearance quality grade discrimination device 1 used in the method according to the present invention is one in which an imaging signal for a plurality of grains acquired in the imaging means 2 is sent to the quality grade discrimination means 4, the quality grade of each of the grains is discriminated in the quality grade discrimination means 4, and a weight ratio by quality grade of the grains is calculated.

The grain appearance quality grade discrimination device used in the method according to the present invention is not limited to one comprising a scanner or other imaging means for simultaneously imaging a plurality of grains, as long as the device is one in which at least rice, wheat, bean, corn, or another grain is imaged and the quality grade of the grain is discriminated on the basis of the imaging data. The grain appearance quality grade discrimination device used in the method according to the present invention may be one in which, e.g., grains are individually imaged as with the grain quality grade discrimination device described in JP-A 2008-298695.

A description will now be given of a method for calculating the weight ratio by quality grade of grains using the grain appearance quality grade discrimination device according to the present invention.

Figure 2:
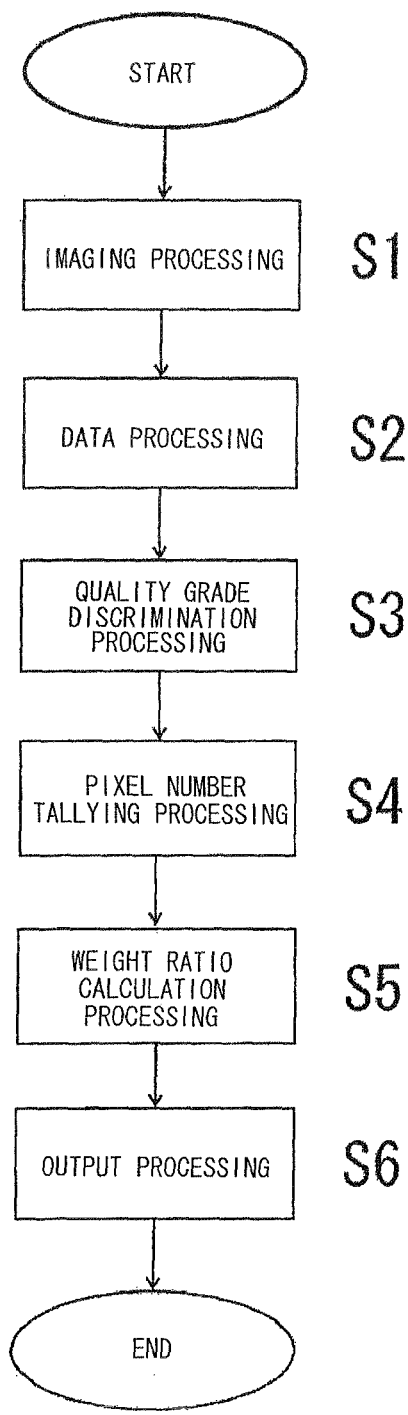
FIG. 2 is a flow chart showing the calculation of the weight ratio by quality grade of grains according to the method of the present invention.
Figure 6:
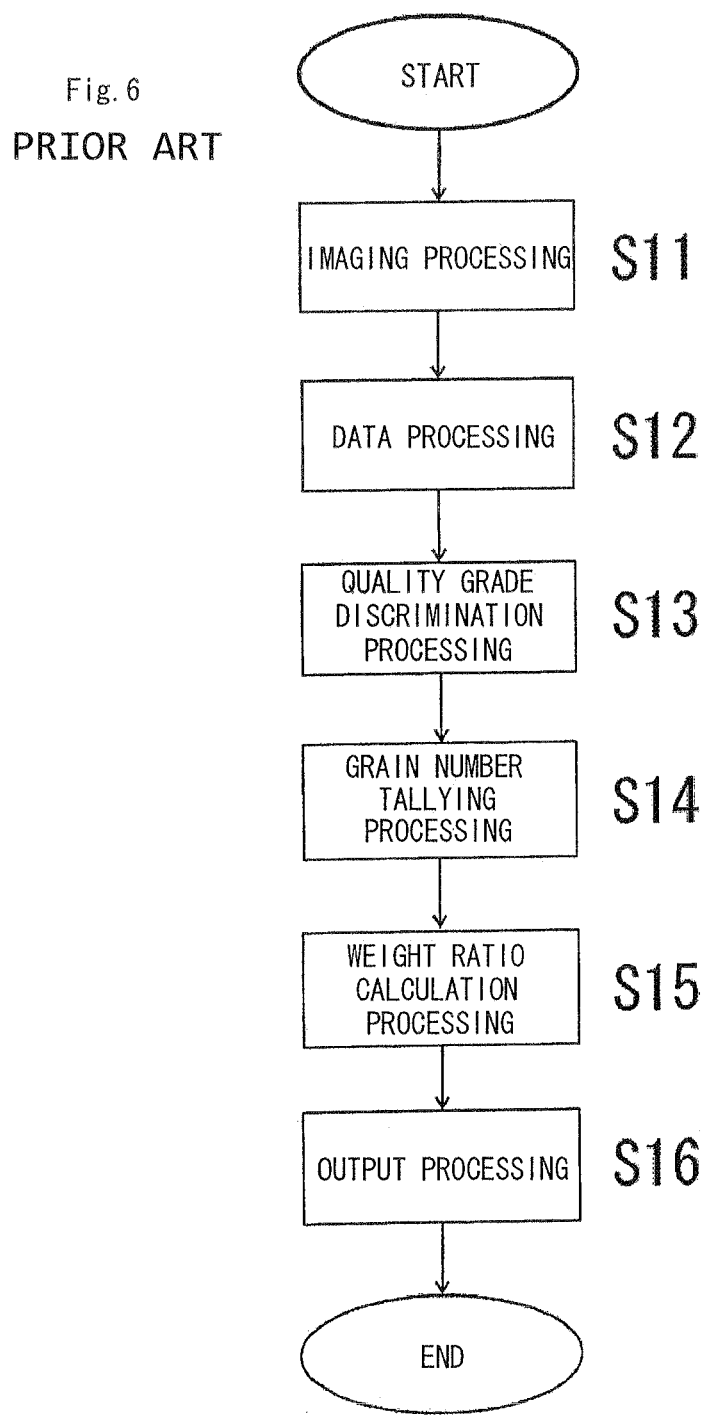
FIG. 6 is a flow chart showing the calculation of the weight ratio by quality grade of a grain according to a conventional method.

FIG. 2 shows a workflow of the present invention for calculating the weight ratio by quality grade of unpolished rice using grain appearance quality grade discrimination device 1.

The method according to the present invention is initiated by placing the imaging tray 5 accommodating a plurality of sample unpolished rice grains onto the imaging platform 2b of the imaging means 2.

(1) Imaging Processing (S1)

First, the grain appearance quality grade discrimination device 1 uses the imaging means 2 to image a plurality of sample grains accommodated on the imaging tray 5, and acquires imaging data for the sample grains.

(2) Data Processing (S2)

Next, the grain appearance quality grade discrimination device 1 sends the acquired imaging data to the quality grade discrimination means 4, and performs image processing to extract information relating to the profile shape, area, length, width, color, cracking, and other quality grades of the sample grains.

(3) Quality Grade Discrimination Processing (S3)

The grain appearance quality grade discrimination device 1 then compares, in the quality grade discrimination means 4, the information relating to the quality grade with a threshold value that has been predetermined; and discriminates the quality grade of each of the sample grains.

(4) Pixel Number Tallying Processing (S4)

The grain appearance quality grade discrimination device 1 tallies by quality grade, in the quality grade discrimination means 4, the number of pixels for the sample grains for which the quality grade has been discriminated, on the basis of the profile shape.

(5) Weight Ratio Calculation Processing (S5)

The grain appearance quality grade discrimination device 1 calculates the weight ratio by quality grade on the basis of the number of pixels corresponding to the sample grains tallied by quality grade in the quality grade discrimination means 4 and the weight conversion coefficient (dot weight) per pixel that has been predetermined by quality grade.

(6) Output Processing (S6)

Lastly, the grain appearance quality grade discrimination device 1 outputs, to the display, a calculated value for the weight ratio by quality grade of the sample grains.

The method according to the present invention is ended at a stage where the grain appearance quality grade discrimination device 1 has ended discrimination of the quality grade for all sample grains, tallied the number of pixels by quality grade for all sample grains, and calculated the weight ratio by quality grade for all sample grains.

Each of the above-mentioned processes performed on a plurality of unpolished rice grains may be performed in parallel or as a batch.

FIG. 3 shows a comparison of the two broken grains shown in FIG. 8, made at pixel level.

In an instance in which the two grains are compared in terms of the number of pixels as shown in FIG. 3, it can be seen that FIG. 3(*a*) corresponds to 569 pixels and FIG. 3(*b*) corresponds to 74 pixels, and that the respective sizes differ by approximately threefold.

According to the above-mentioned method of the present invention, it becomes possible to calculate the weight ratio taking the size variation into consideration with regards to unpolished rice grains classified into the same quality grade.

FIG. 4 shows an example of calculating the weight ratio by quality grade of unpolished rice grains according to the above-mentioned method of the present invention. In FIG. 4, the quality grade of unpolished rice grains is represented as "discrimination classification".

In the present invention, there is stored and configured in advance, in the quality grade discrimination means 4 of the grain appearance quality grade discrimination device 1, a weight conversion coefficient (dot weight) per pixel of unpolished rice by discrimination classification (quality grade).

The grain appearance quality grade discrimination device 1 multiplies the number of dots (number of pixels) of the sample grains, tallied by discrimination classification (quality grade), by the weight conversion coefficient (dot weight), thereby determining the converted weight; and calculates the proportion of the converted weight in relation to the total weight as a weight ratio by discrimination classification (quality grade).

The "weight conversion coefficient (dot weight)" in FIG. 4 is entered by rounding a lower-level value up or down. Therefore, the calculated value of the "converted weight" is somewhat different from that in reality.

The weight conversion coefficient (dot weight) per pixel of unpolished rice shown in FIG. 4 can be determined in advance by using the actual weight of unpolished rice classified by quality grade and the number of dots (number of pixels) of unpolished rice classified by quality grade tallied in the grain appearance quality grade discrimination device. Determining a weight conversion coefficient by location of production of the unpolished rice, by variety, or by a combination of location of production and variety makes it possible to calculate the weight ratio by quality grade, using the method of the present invention, in a more accurate manner.

FIG. 5 shows another example of calculating the weight ratio by quality grade of grains according to the method of the present invention. In FIG. 5, the quality grade of unpolished rice is represented as "discrimination classification".

In the example shown in FIG. 4, unpolished rice is used as the grain. However, according to the method of the present invention, it is also possible to calculate the weight ratio by quality grade of polished rice or another grain in an accurate manner.

Also, in the example shown in FIG. 4, an evaluation classification used for unpolished rice in Japan is used as the discrimination classification (quality grade). However, according to the method of the present invention, another evaluation classification, in particular an evaluation classification used in China or another country can similarly be used to calculate the weight ratio by quality grade of grains in an accurate manner. It shall be apparent that in such an instance, a setting is made in advance in the quality grade discrimination means 4 of the grain appearance quality grade discrimination device 1, in relation to a variety of threshold values used to discriminate the quality grade in relation to the evaluation classification, and a weight conversion coefficient (dot weight) per pixel of the grains, determined in correspondence with each of the quality grades.

In the above-mentioned method of the present invention, the grain size is taken into account in the weight conversion coefficient (dot weight) per pixel of the grains. However, it is preferable that [the weight conversion coefficient (dot weight)] includes thickness information in addition to the grain size in terms of calculating the weight ratio by quality grade in an accurate manner.

In the above-mentioned method of the present invention, the grain size is taken into account in the weight conversion coefficient (dot weight) per pixel of the grains. However, color information regarding the grains can also be added. If the weight conversion coefficient (dot weight) per pixel of the grains is one to which color information regarding the grains has been added, it is possible to calculate the weight ratio by quality grade in an even more accurate manner.

Examples of calculating the weight ratio by quality grade of grains according to the above-mentioned method of the present invention relate to unpolished rice and polished rice. However, it shall be apparent that the weight ratio by quality grade can be calculated in a similar manner in relation to wheat, bean, corn, or another grain.

It shall be apparent that the configuration of the present invention is not limited to the embodiment described above; it can be changed as appropriate without departing from the scope of the invention.

INDUSTRIAL APPLICABILITY

The method for calculating the weight ratio by quality grade of rice, wheat, bean, corn, or another grain according to the present invention is one in which it is possible to calculate the weight ratio in an accurate manner even in an instance in which the weight ratio is calculated using results of quality discrimination performed by the grain appearance quality grade discrimination device, and is one that has an extremely high utility value.

KEY

1 Grain appearance quality grade discrimination device
2 Imaging means (scanner)
3 Cable
4 Quality grade discrimination means (PC)
5 Imaging tray
11, 12 Broken grain
15 Pixel

The invention claimed is:

1. A method for calculating a weight ratio by quality grade using a grain appearance quality grade discrimination device for imaging grains using an imager and discriminating the quality grade of the grains on the basis of data of the imaged grains; the method for calculating a weight ratio by quality grades using a grain appearance quality grade discrimination device characterized in comprising:
    imaging a plurality of grains;
    discriminating the quality grades of said grains on the basis of data of the imaged grains;
    tallying, by quality grade, the number of pixels in said data of the imaged grains with regards to the grains whose quality grade has been discriminated;
    multiplying the number of pixels tallied by quality grade by a weight conversion coefficient per pixel predetermined by quality grades, by location of production, by variety, and thereby converting said number of pixels into a weight by quality grade; and
    calculating the weight ratio by quality grade of the grains on the basis of the weight by quality grade.

2. The method according to claim 1, wherein the imager for imaging said grains is an image-reading device.

3. The method according to claim 1, wherein the imager is a scanner.

* * * * *